(12) United States Patent
Schoendorf

(10) Patent No.: US 8,897,886 B2
(45) Date of Patent: Nov. 25, 2014

(54) DEVICE FOR ELECTROTHERAPEUTIC TREATMENT

(75) Inventor: Erhard Schoendorf, Wadgassen (DE)

(73) Assignees: Robert Ley, Clemency (LU); Ralf Scherer, Heusweiler (DE)

( * ) Notice: Subject to any disclaimer, the term of this patent is extended or adjusted under 35 U.S.C. 154(b) by 0 days.

(21) Appl. No.: 13/512,510

(22) PCT Filed: Nov. 24, 2010

(86) PCT No.: PCT/DE2010/001385
§ 371 (c)(1),
(2), (4) Date: Jun. 19, 2012

(87) PCT Pub. No.: WO2011/063797
PCT Pub. Date: Jun. 3, 2011

(65) Prior Publication Data
US 2012/0259395 A1 Oct. 11, 2012

(30) Foreign Application Priority Data

Nov. 30, 2009 (DE) .......................... 10 2009 056 095

(51) Int. Cl.
*A61N 1/00* (2006.01)
*A61N 1/32* (2006.01)
*A61N 1/36* (2006.01)

(52) U.S. Cl.
CPC ............. *A61N 1/323* (2013.01); *A61N 1/36014* (2013.01)
USPC ................................. 607/115; 607/68; 607/69

(58) Field of Classification Search
USPC ............................................. 607/68, 69, 115
See application file for complete search history.

(56) References Cited

U.S. PATENT DOCUMENTS

| | | | | |
|---|---|---|---|---|
| 5,476,481 | A | * | 12/1995 | Schondorf .......................... 607/2 |
| 2002/0099425 | A1 | | 7/2002 | Johnson et al. |
| 2006/0052844 | A1 | | 3/2006 | Newman |
| 2006/0195153 | A1 | | 8/2006 | DiUbaldi |

FOREIGN PATENT DOCUMENTS

| | | |
|---|---|---|
| DE | 30 10 716 A1 | 9/1981 |
| EP | 0 612 259 | 8/1994 |
| FR | 2 493 154 | 5/1982 |

OTHER PUBLICATIONS

International Search Report of PCT/DE2010/001385, Apr. 21, 2011.

* cited by examiner

*Primary Examiner* — Nicole F Lavert
(74) *Attorney, Agent, or Firm* — Collard & Roe, P.C.

(57) ABSTRACT

The invention relates to an apparatus for electrotherapeutic treatment of the human body, which has electrodes that can be laid against the body and a device for producing a therapy current that flows through the body, by way of the electrodes, whereby the device for generating the therapy current comprises two oscillators having frequencies $f_1$ and $f_2$ that lie close to one another and are suitable for forming a beat, an oscillator having a frequency $f_3$ that is less than the beat frequency $f_{s1} = f_1 - f_2$, and a mixer device for superimposition of the oscillator signals. According to the invention, the device for producing the therapy current comprises at least two additional oscillators with frequencies $f_4$ and $f_5$, and the mixer device is provided with frequencies $f_1$ to $f_5$ for superimposition of all oscillators.

9 Claims, 1 Drawing Sheet

DEVICE FOR ELECTROTHERAPEUTIC TREATMENT

CROSS REFERENCE TO RELATED APPLICATIONS

This application is the National Stage of PCT/DE2010/001385 filed on Nov. 24, 2010, which claims priority under 35 U.S.C. §119 of German Application No. 10 2009 056 095.5 filed Nov. 30, 2009, the disclosure of which is incorporated by reference. The international application under PCT article 21(2) was not published in English.

BACKGROUND OF THE INVENTION

1. Field of the Invention

The invention relates to an apparatus for electrotherapeutic treatment of the human body, which has electrodes that can be laid against the body and a device for producing a therapy current that flows through the body, by way of the electrodes, whereby the device for generating the therapy current comprises two oscillators having frequencies $f_1$ and $f_2$ that lie close to one another and are suitable for forming a beat, an oscillator having a frequency $f_3$ that is less than the beat frequency $f_{s1}=f_1-f_2$, and a mixer device for superimposition of the oscillator signals.

2. Prior Art

Such an apparatus is evident from EP 0 612 259 B1. Two alternating fields having frequencies of about 4000 Hz are superimposed to form a beat having a frequency between 1 and 100 Hz. A gradual change in polarity of the basic frequency is produced by means of superimposition of these alternating fields with a third alternating field, the frequency of which amounts to between 0.1 and 5 Hz, and muscles, nerves, and vascular tissue are stimulated in the manner of direct current, with successively reversing polarity.

SUMMARY OF THE INVENTION

The invention is based on the task of increasing the efficacy of the electrotherapeutic treatment, while maintaining good skin tolerance.

According to the invention, this task is accomplished in that the device for generating the therapy current comprises at least two further oscillators having frequencies $f_4$ and $f_5$, whereby the mixer device is provided for superimposition of the signals of all the oscillators having the frequencies $f_1$ to $f_5$.

Surprisingly, it has been shown that it is possible to use greater currents using the apparatus according to the invention, without burning pains or burn reactions occurring in a treated person at the locations of the skin on which the electrodes are sitting. As a result, the treatment period can be shortened. The inventor has found that the skin tolerance is significantly improved by means of the interaction of the oscillators, and that furthermore, even regions that lie deeper in the body can be stimulated.

The use of the two further oscillators furthermore makes it possible to stimulate the muscles, the nerves, and the tissue in different frequency ranges. In particular, the lymph circulation can be stimulated with a frequency range of 0.1 to 3 Hz; chronic pain can be relieved at 1 to 30 Hz, and acute pain can be relieved at about 100 Hz.

Furthermore, aside from muscle and nerve stimulation, the ion milieu in the tissue is also positively influenced for healing.

It is imaginable to achieve additional advantages in treatment by means of superimposition with additional oscillators. Stimulation could take place in additional frequency ranges, in targeted manner.

In an embodiment of the invention, the frequencies $f_4$ and $f_5$ are suitable for forming a beat, whereby the beat frequency $f_{s2}=f_4-f_5$ is greater than the beat frequency $f_{s1}$.

In another embodiment of the invention, the frequency $f_{s1}$ amounts to 0.1 to 5 Hz, preferably 0.1 to 2 Hz, and the frequencies $f_1$ and $f_2$ amount to between 3000 and 5000 Hz, preferably between 4000 and 4400 Hz. Because treatment at these frequencies has slight effects on the pain receptors of the skin, it is not felt to be unpleasant by the persons being treated.

It is practical if the frequency $f_{s2}$ amounts to 1 to 100 Hz, and the frequencies $f_4$ and $f_5$, respectively, also lie in the range already mentioned, of 3000 to 5000 Hz, preferably 4000 to 4400 Hz.

In another embodiment of the invention, the frequency $f_3 \leq (f_1-f_2)/2$. Stimulation in the manner of direct current is achieved, at least for a certain period of time, by means of the change in polarity that is generated in this way and takes place at a lesser frequency, in comparison with the beats $f_{s1}$ and $f_{s2}$.

It is practical if the frequency $f_3=(f_1-f_2)/n$, whereby n are whole numbers $\geq 2$. In the case of corresponding synchronization of the oscillators, the result can be achieved, in this manner, that complete beat bulges of the beat frequency $f_{s1}$ are always shifted into the positive or negative range by means of the superimposition with the oscillator having the frequency $f_3$.

Particularly advantageous treatment results can be achieved with the electrostimulation therapy if the amplitude of the signal of the oscillator having the frequency $f_3$ amounts to three times the amplitude that results from superimposition of the other oscillator signals. In this way, it is made possible that the resulting signal that is obtained from superimposition of the oscillator signals is shifted completely into the positive or negative range for a certain period of time.

Electrochemical effects of the electrostimulation therapy can now be utilized better, whereby an undesirable permanent shift of ions in only one direction, as is the case for treatment with direct current, is avoided. Furthermore, the function of osmosis and diffusion on membranes in the body tissue can be improved by means of this movement of the ions.

It is practical if the amplitudes of the oscillator signals having the frequencies $f_4$ and $f_5$ are less, in each instance, than those having the frequencies $f_1$ and $f_2$.

In an embodiment of the invention, a first mixer of the mixer device is provided for superimposition of the oscillation signals having the frequencies $f_1$ and $f_2$. In this way, the beat frequency can be precisely adjusted. Furthermore, a second mixer is provided for superimposition of the signals output by the first mixer and the signals of the other oscillators.

It is practical if the device furthermore comprises an amplifier for the signals output by the second mixer.

BRIEF DESCRIPTION OF THE DRAWINGS

The invention will be explained in greater detail below, using an exemplary embodiment and the attached drawings that relate to this exemplary embodiment. These show.

DETAILED DESCRIPTION OF THE PREFERRED EMBODIMENTS

Figure 1:
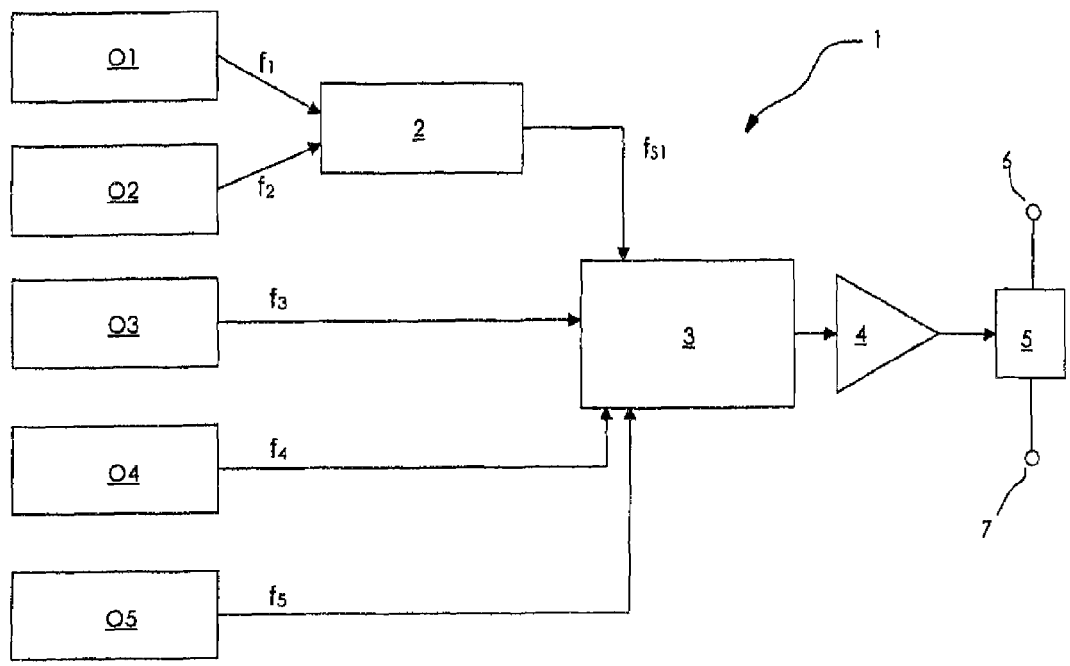
FIG. 1 a circuit schematic for an apparatus according to the invention.

A schematic of a circuit of a device 1 for applying current to electrodes 6, 7 of an apparatus according to the invention is shown in FIG. 1. It shows five oscillators $O_1$, $O_2$, $O_3$, $O_4$, and $O_5$, two mixers 2 and 3, an amplifier 1, as well as an output 5 for the electrodes 6 and 7. The signals of the oscillators $O_1$ and $O_2$, which have a frequency $f_1$ and $f_2$, respectively, are superimposed in the mixer 2, whereby a beat frequency $f_{s1}$ is formed.

The signals output by the mixer 2 as well as the signals of $O_3$, $O_4$, and $O_5$ are superimposed in the second mixer 3. An amplifier 4 is provided for an output signal of the mixer 3, which amplifier outputs a therapy current to the electrodes 6 and 7, by way of the output 5.

The signals of $O_1$ to $O_5$ are normally output as sine oscillations. However, other shapes, such as triangular or rectangular oscillations, for example, are also possible.

Figure 2:
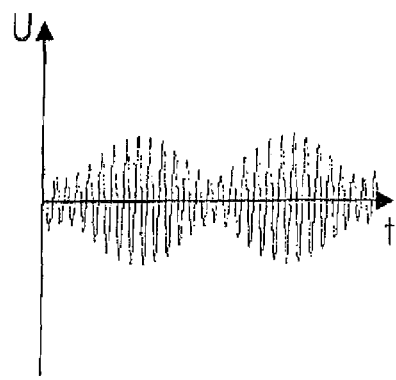
FIG. 2 in a diagram, signals of a first mixer of the apparatus.

In FIG. 2, a voltage/time diagram of the signal output by the mixer 2 is shown. It shows a beat having the frequency $f_{s1}=1$ Hz, and results from the superimposition of the signals of $O_1$ and $O_2$ at a frequency of $f_1$-4000 Hz and $f_2$=3999 Hz, respectively. By means of corresponding adjustment of the frequencies $f_1$ and $f_2$, it is possible to change the frequency of the beat between 0.1 and 3 Hz, and to adapt it as required by the treatment, particularly for stimulation of the lymph circulation.

The frequencies $f_4$ and $f_5$ of the signals $O_4$ and $O_5$ amount to 4010 Hz and 4040 Hz, respectively, and are superimposed to form a beat frequency $f_{s2}$ of 30 Hz, in other words in the range for treatment of chronic pain. Here, too, different beat frequencies $f_{s2}$ between 1 and 100 Hz can be adjusted, by means of a corresponding change in the frequencies $f_4$ and $f_5$, depending on the treatment goal being pursued.

Figure 3:
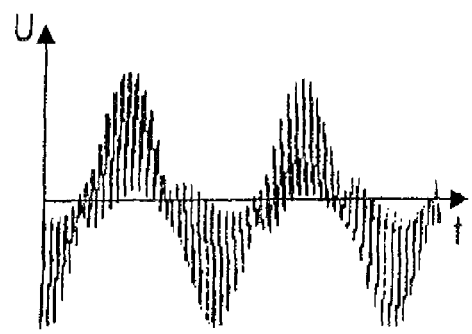
FIG. 3 in a diagram, signals of a second mixer of the apparatus.

As is evident from FIG. 3, the overall signal output by the mixer 3 can be shifted completely into the positive or negative range, particularly by means of adjustment of the value of the signal of $O_3$ to three times the voltage that results from superimposition of the signals of $O_1$, $O_2$, $O_4$, and $O_5$.

The frequency $f_3$ determines the duration with which a voltage output by the amplifier 4 flows on the body in the specific direction, and, in the present exemplary embodiment, amounts to 0.5 Hz and thus to half the frequency $f_{s1}$.

It is therefore possible to conduct treatment in the manner of direct current, at great effect, at least for short periods of time, without pain or actually burns occurring at locations of the skin on which the electrodes are sitting.

The invention claimed is:

1. Apparatus for electrotherapeutic treatment of a human body,
    which has a unit for producing a therapy current that flows through the body and electrodes that are connected to the unit and that can be laid against the body for conducting the therapy current,
    wherein the unit comprises two oscillators having frequencies $f_1$ and $f_2$ that lie close to one another and are suitable for forming a beat, an oscillator having a frequency $f_3$ that is less than a beat frequency $f_{s1}=f_1-f_2$, and
    a mixer device for superimposition of the oscillator signals,
    wherein for improving the skin tolerance of the treatment and for stimulating regions that lie deep in the body the unit for generating the therapy current comprises at least two further oscillators having frequencies $f_4$ and $f_5$, and
    the mixer device is provided for superimposition of the signals of all the oscillators having the frequencies $f_1$ to $f_5$, wherein the frequencies $f_4$ and $f_5$ which are suitable for forming a beat frequency $f_{s2}$ that is greater than $f_{s1}$.

2. Apparatus according to claim 1, wherein
an amplifier (4) is provided for a signal output by the mixer device.

3. Apparatus according to claim 1, wherein
the mixer device comprises a first mixer (2) for superimposition of the oscillator signals having the frequencies $f_1$ and $f_2$ and a second mixer (3) for superimposition of a signal of the first mixer (2) with the oscillator signals having the frequencies $f_3$, $f_4$, and $f_5$.

4. Apparatus according to claim 1, wherein
the mixer device is provided for addition of the signals.

5. Apparatus according to claim 1, wherein
the beat frequency $f_{s1}$ amounts to 0.1 to 5 Hz, preferably 0.1 to 2 Hz, and/or the beat frequency $f_{s2}$ amounts to 1 to 100 Hz.

6. Apparatus according to claim 1, wherein
the frequencies $f_1$ and $f_2$ and/or the frequencies $f_4$ and $f_5$ amount to 3000 to 5000 Hz, preferably 4000 to 4400 Hz.

7. Apparatus according to claim 1, wherein
the frequency $f_3 \leq (f_1-f_2)/2$.

8. Apparatus according to claim 1, wherein
the amplitude of the oscillator signal having the frequency $f_3$ can be adjusted to at least three times the amplitude forms as the result of superimposition of the oscillator signals having the frequencies $f_1$, $f_2$, $f_4$, and $f_5$.

9. Apparatus according to claim 1, wherein
the amplitudes of the oscillator signals having the frequencies $f_4$ and $f_5$ are less, in each instance, than those having the frequencies $f_1$ and $f_2$.

* * * * *